United States Patent
Arand et al.

[11] Patent Number: 5,318,036
[45] Date of Patent: Jun. 7, 1994

[54] METHOD AND APPARATUS FOR REMOVING BASELINE WANDER FROM AN ECG SIGNAL

[75] Inventors: Patricia Arand; Tim LaCroix, both of McMinnville, Oreg.

[73] Assignee: Hewlett-Packard Company, Palo Alto, Calif.

[21] Appl. No.: 853,687

[22] Filed: Mar. 17, 1992

[51] Int. Cl.$^5$ .............................. A61B 5/0428
[52] U.S. Cl. ................... 128/696; 128/901
[58] Field of Search ............. 128/695, 696, 702, 703, 128/704, 705, 710, 901, 902; 364/413.06

[56] References Cited

U.S. PATENT DOCUMENTS

| | | | |
|---|---|---|---|
| 4,422,459 | 12/1983 | Simson | 128/702 |
| 4,458,691 | 7/1984 | Netravali | 128/705 |
| 4,458,692 | 7/1984 | Simson | 128/705 |
| 4,492,235 | 1/1985 | Sitrick | 128/705 |
| 5,025,724 | 6/1991 | Albert et al. | 128/696 |
| 5,117,833 | 6/1992 | Albert et al. | 128/702 |

OTHER PUBLICATIONS

David W. Mortara, *Digital Filters for ECG Signals*, Computers in Cardiology, pp. 511–514 (IEEE, 1977).
Gradwohl, J. R., et al., *Comparison of Two Methods for Removing Baseline Wander*, Computers in Cardiology, pp. 493–496 (IEEE, 1988).
Franket et al., *A Filter to Suppress ECG Baseline Wander and Preserve ST-Segment Accuracy in a Real-time Environment*, Journal of Electrocardiology, vol. 24, No. 4, pp. 315–323 (Oct. 4, 1991).
Pottala et al., *Suppression of Baseline Wander in the ECG Using a Bilinearly Transformed, Null-phase Filter*, Journal of Electrocardiology, vol. 22 Supp.

*Primary Examiner*—Lee S. Cohen
*Assistant Examiner*—Jeffrey R. Jastrzab

[57] ABSTRACT

A method and apparatus for removing baseline wander in which an ECG waveform is continuously sampled at 500 samples per second. The digitized data is continuously filtered by an infinite-impulse response (IIR) filter implemented on a first microprocessor. The data is stored in a buffer from which it is read in reverse chronological order in overlapping 3 second blocks. Each block is applied to the input of a second IIR filter which is implemented on a second microprocessor with substantially the same code as the first IIR filter. The first 1.5 seconds of each reverse-filtered block is disregarded to permit the output of the filter to settle. The retained data is stored in a queue from which it is read and displayed on a monitor or printed with baseline wander removed.

18 Claims, 7 Drawing Sheets

FIG. 7

METHOD AND APPARATUS FOR REMOVING BASELINE WANDER FROM AN ECG SIGNAL

BACKGROUND OF THE INVENTION

1. Field of the Invention

The present invention relates generally to methods and apparatus for removing baseline wander from an ECG signal and more particularly to such methods and apparatus which utilize a filter having a nonlinear phase response.

2. Description of the Related Art

In the collection and analysis of ECG waveforms, electrodes are connected to a patient for detecting the ECG signal. Sometimes the signal is provided to a Holter monitor which is a recording device worn by the patient. After data is collected for a predetermined length of time, it is transferred to a system which analyzes and displays the collected data. Such a system is suitable for diagnosing certain types of heart conditions. In some situations, however, it is necessary and desirable for a clinician to observe the ECG waveform on a real-time basis. For example, when a patient is being monitored during a stress test it is critical that a clinician observe the ECG waveform substantially as it occurs in case changes in the waveform indicate a condition which would require the test to be varied or stopped altogether.

The baseline of an ECG waveform can vary considerably. Such variations are known as baseline wander. Baseline wander can be caused by, e.g., respiration, poor electrode contact and sweating. There are both high and low amplitude wanders across a range of frequencies. Because the spectra of baseline wander and the ECG signal are very close, and in some cases may overlap, it is difficult to eliminate the wander and leave the ECG signal undistorted, especially when real-time monitoring is required.

There is a prior art technique for removing baseline wander known as the cubic spline method. Using this method, baseline wander is estimated with a third order polynomial and the estimate is subtracted from the ECG signal. This method has a number of disadvantages. To generate the estimate, three data points on an ECG waveform, called knots, are located. The knots are typically located on the PR segments of three consecutive heartbeats in an ECG waveform. Beat times generated by a QRS detector are used to locate the PR segments. Because all QRS detectors sometimes produce false beat times, the ECG is distorted when a data point is derived from a false beat. In addition, in the presence of high noise, the QRS detector may not function. Also, baseline wander with sharp transitions may not be accurately described by a cubic polynomial. The processing delay between the real-time ECG waveform and the corrected waveform varies dependent upon heart rate. The inherent delay is three beats since information from three consecutive beats is needed before the baseline estimate between the first two can be computed. For example, at a heart rate of 60 beats per minute, the delay is at least three seconds.

In addition to the cubic spline method, there are prior art filtering techniques for removing baseline wander from an ECG waveform. Two filters which have been used to filter ECG waveforms include a finite-impulse response (FIR) filter and an infinite-impulse response (IIR) filter. Both FIR and IIR filters can be described by equations having a preselected number of variables and corresponding coefficients which together define the operating characteristics of the filter. The more filter coefficients, the more computations are required to produce a single output data point.

The American Heart Association (AHA) and the Association for Advancement of Medical Instrumentation (AAMI) now suggest 0.67 Hz as the cut-off point of a high-pass baseline wander filter. Any filter for removing baseline wander from an ECG waveform must have a sharp transition region. FIR filters are disadvantageous because many coefficients are necessary to achieve a sharp transition region.

IIR filters, on the other hand, can achieve a sharp transition region with a small number of coefficients. However, an IIR filter which has a cut-off frequency high enough to remove baseline wander has a nonlinear phase response which distorts meaningful components of the ECG waveform. In one paper, David W. Mortara, *Digital Filters for ECG Signals*, Computers in Cardiology, Pages 511-514 (IEEE, 1977), an IIR filter is described which has a high cut-off frequency which therefore causes less low frequency distortion. This filter, however, has gain in the pass band. Thus, any baseline wander having a frequency which falls in the pass band may be emphasized.

In Erik W. Pottala, et al., *Suppression of Baseline Wander in the ECG Using a Bilinearly Transform, Null-Phase Filter*, Journal of Electrocardiology 22 (Suppl):244(1989), a filter having a nonlinear phase response is used to filter an ECG waveform. This filter filters the data both forward and backward in time thereby removing nonlinearities injected by the filter. The problem with utilizing this technique is that the filtered signal is not available until after it has been filtered both forward and backward. Thus, prior art filters utilize forward and reverse-time filtering only in the context of removing baseline wander from ECG by running a predetermined length of data, e.g., five seconds worth, first in a forward direction through a filter and thereafter in a reverse-time direction thereby removing baseline wander. Such filtering is not suitable for situations in which near real-time monitoring is required.

SUMMARY OF THE INVENTION

A method for removing baseline wander from an ECG signal in which the ECG signal is applied to a filter having a nonlinear phase response which produces filtered-signal data. The data is stored and blocks of the stored data are applied in time reversed order to the nonlinear filter thereby producing reverse-filtered blocks. Each reverse-filtered block is displayed in chronological order.

In another aspect of the invention, the blocks of stored data applied in time reversed order to the filter overlap each other in time and the first portion of the reverse-filtered block is discarded because it falls within the settling time of the filter.

The present invention provides the advantages of an easily implemented IIR filter while removing any nonlinearities injected by the filter and displaying ECG signal with baseline wander removed therefrom on a near real-time basis.

The foregoing and other objects, features and advantages of the invention will become more readily apparent from the following detailed description of a preferred embodiment which proceeds with reference to the drawings.

DETAILED DESCRIPTION OF THE PREFERRED EMBODIMENT

Figure 1:
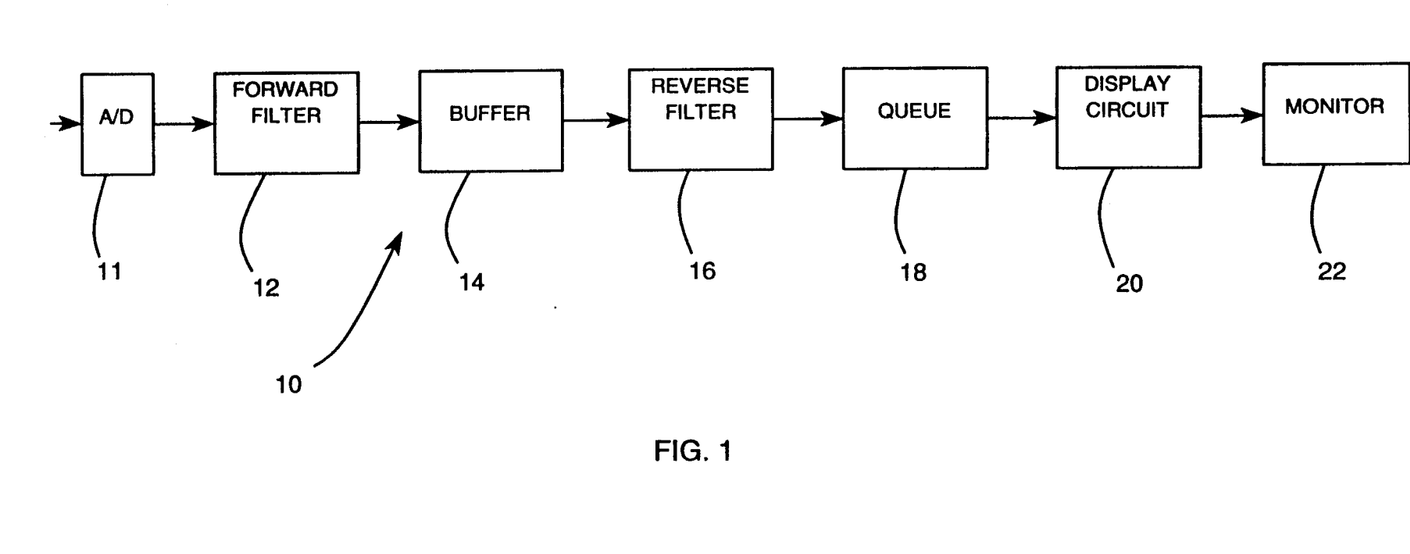
FIG. 1 is a schematic diagram of an apparatus constructed in accordance with the present invention.

Turning now to the drawings and particularly with reference to FIG. 1, indicated generally at 10 is a schematic diagram of a system for displaying an ECG signal with baseline wander removed. Included in system 10 is an analog-to-digital converter 11, a forward filter 12, such being also referred to herein as a first filter, a buffer 14 and a reverse filter 16, also referred to herein as a second filter. Filters 12, 16 are referred to herein as nonlinear filters. As used herein the term "nonlinear filter" refers to a filter having a nonlinear phase response. In the present embodiment of the invention, filter 12 comprises a second order infinite-impulse response (IIR) filter characterized by the following equation:

$$a_0 y(i) = b_0 x(i) + b_1 x(i-1) + b_2 x(i-2) - a_1 y(i-1) - a_2 y(i-2)$$

where a and b are filter coefficients, x(i) is an ECG sample value, x(i−1) is the previous ECG sample value and x(i−2) is the ECG sample value occurring before x(i−1). The filter output signal is y(i), with y(i−1) and y(i−2) being the previous two filter output values. When analog-to-digital converter 11 samples at 500 samples per second, as is the case with the present embodiment, the filter coefficients are as follows:

$b_0 = 0.99518889087062$
$b_1 = -1.99037778174124$
$b_2 = b_0$
$a_0 = 1.0$
$a_1 = -1.99035274726943$
$a_2 = 0.99040281621305$

In the present embodiment of the invention, IIR filter 12 is implemented by computer code. A person having ordinary skill in the art of implementing IIR filters in computer code could, based upon the above equation, sampling rate and coefficient values, write appropriate code for implementing the filter. It should be noted that the coefficients must be converted to the appropriate numerical precision for the particular microprocessor with which the program is utilized to implement the invention.

In the present embodiment of the invention, reverse filter 16 comprises a filter which is substantially identical to filter 12. It is implemented by the same code on a separate microprocessor.

As can be seen in FIG. 1, digitized ECG data from converter 11 is filtered by filter 12 and written into a buffer 14 which in the present embodiment of the invention comprises conventional random access memory (RAM). Reverse filter 16 reads filtered data from buffer 14 in reverse chronological order, filters the same and, as will later be seen in more detail, stores a portion of the reverse-filtered data in a queue 18. Queue 18 also comprises conventional RAM. The reverse-filtered data is read from the queue by conventional video display circuitry 20 and supplied in a known manner to a monitor 22 upon which the ECG waveform having baseline wander removed therefrom can be observed.

It should be appreciated that as used herein the term ECG signal or waveform may refer to the analog signal applied to converter 11 from a patient or to be digitized analog signal processed by filters 12, 16 or to the signal with baseline wander removed displayed on monitor 22.

Figure 5:
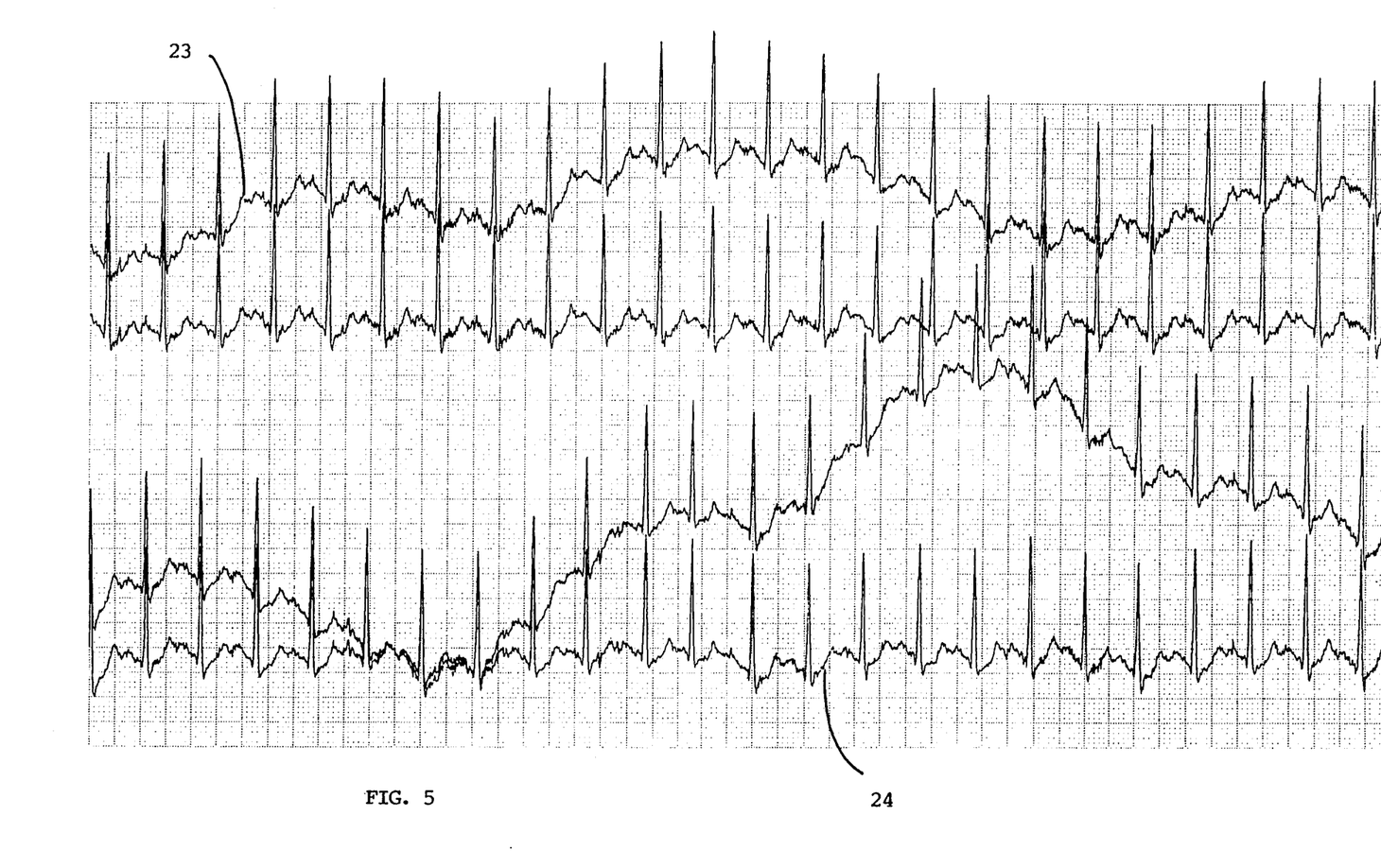
FIG. 5 comprises printed ECG waveforms uncorrected and with baseline wander removed.

Consideration will now be made to the manner in which system 10 operates to remove baseline wander. First, with reference to FIG. 5, an ECG waveform 23 having evident baseline wander proceeds from left to right and top to bottom in FIG. 5. It is printed above a corrected ECG waveform 24, also proceeding from left to right and top to bottom, immediately beneath waveform 23. Waveform 24 comprises waveform 23 after the same is processed by system 10 to remove baseline wander. The waveforms are printed in FIG. 5 synchronized in time, i.e., the data points comprising waveform 24 are directly beneath corresponding data points in waveform 23 after the same are processed to remove the effect of baseline wander. With reference to FIG. 1, the uncorrected waveform 23 is applied to the input of converter 11 with corrected waveform 24 being displayed on monitor 22 slightly delayed in time, as is hereinafter explained.

Converter 11 continuously provides digitized ECG to the input of filter 12. Filter 12 continuously filters the digitized data which is written into sequential addresses in buffer 14 under control of a conventional microprocessor (not shown).

Figure 2:
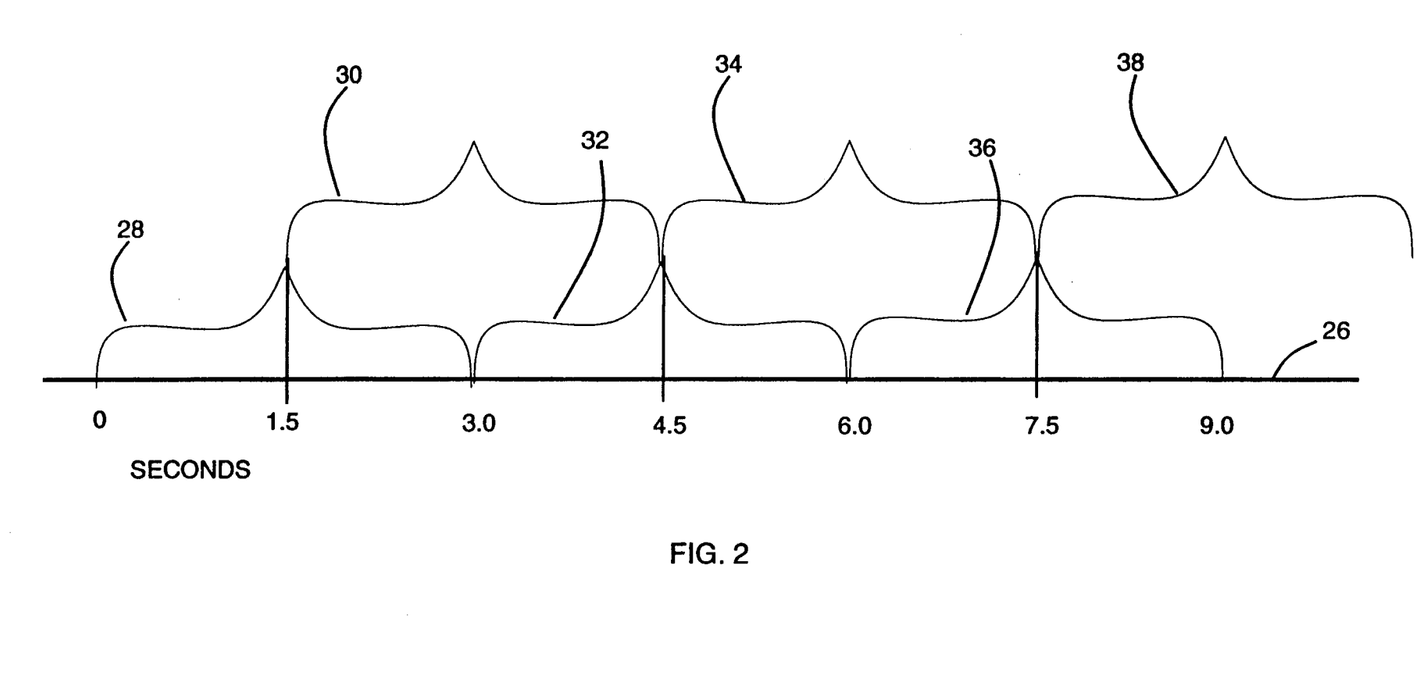
FIG. 2 is a schematic illustrating the data blocks into which the ECG signal is divided in accordance with the preferred embodiment of the present invention.

The code implementing reverse-filter 16 includes a pointer which retrieves data from buffer 14 and applies the same to the input of filter 16. In the present embodiment of the invention, the pointer applies three-second blocks of contiguous data from buffer 14 in reverse chronological order to the input of filter 16. With reference to FIG. 2, a line 26 represents approximately 9 seconds of digitized ECG data stored in buffer 14 in chronological order. The input pointer from filter 16 applies three-second blocks 28, 30, 32, 34, 36, 38, in the foregoing order but with each block being applied in reverse chronological order. For example, as soon as the first three seconds of filtered data, block 28, is stored in buffer 14, the input pointer for filter 16 reads the digitized data beginning at t=3.0 seconds and proceeding to t=0.0 seconds and applies it to the input of filter 16. During this time data from the output of filter 12 continues to be written to buffer 14 in chronological order continuing from t=3.0 seconds.

Because filter 16 has a settling time of approximately 1.5 seconds, the first 1.5 seconds of data output from filter 16, namely from t=3.0 to t=1.5 seconds, is disregarded, i.e., not stored in queue 18. Data processed after the first 1.5 seconds, namely from t=1.5 to t=0.0 seconds, is beyond the settling time and the value therefore is not affected by this filter characteristic. Such data is stored sequentially in queue 18.

As soon as 4.5 seconds of data is stored in buffer 14, the input pointer for reverse-filter 16 begins reading block 30, in reverse chronologic order (from t=4.5 to t=1.5 into the filter. The first 1.5 second output of filter 16, from t=4.5 to t=3.0, is likewise not stored in queue 18 with the remainder of the data being, i.e., that portion from t=3.0 to t=1.5 seconds being stored in queue 18 in order and contiguous with the data from 1.5 to 0.0 seconds which was filtered with block 28.

When the ECG waveform stored in buffer 14 is at the 6 second time in FIG. 2, block 32 is applied in reverse chronological order to the input of filter 16. That portion of the output of filter 16 between t=6.0 and t=4.5 seconds is not stored in queue 18. The output of filter 16 between t=4.5 and t=3.0 seconds is stored contiguously and in chronological order with the previously stored data.

As filtration proceeds as described above, subsequent data written into buffer 14 may be written over previous data which has already been applied to reverse filter 16. Conventional video display circuitry 20 continuously reads data from queue 18 and causes it to be displayed on monitor 22 in a known manner. As the data from queue 18 is displayed, subsequent data written into the queue is written over data which has already been read from queue 18 and displayed on monitor 22. Thus, with reference to FIG. 5, ECG signal 23 is applied to the input of converter 11 with the filtered ECG signal 24 being displayed on monitor 22.

Figure 3:
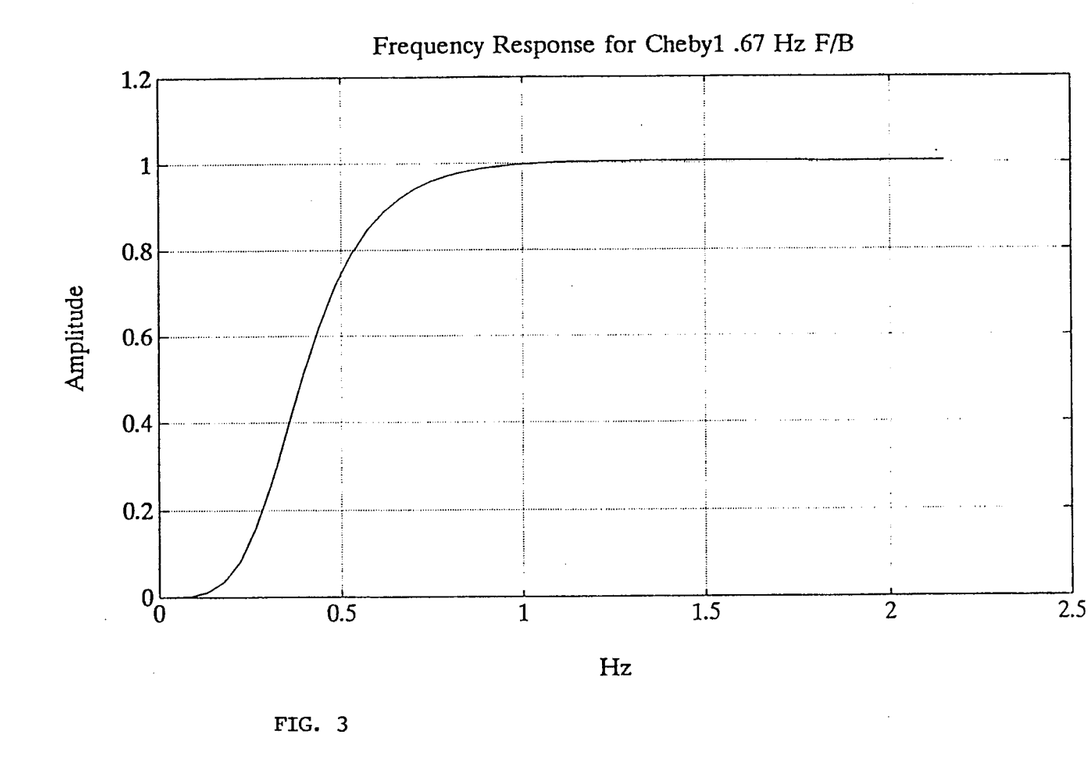
FIG. 3 is a plot of the frequency response of the IIR filter of the preferred embodiment.

FIG. 3 is a plot of the frequency response of the filtration process performed by system 10. In other words, it contrasts frequencies in the data applied to the input of filter 12 with the frequencies of data in queue 18. There is no gain in the passband and the filter cutoff is at 0.67 Hz.

Figure 4:
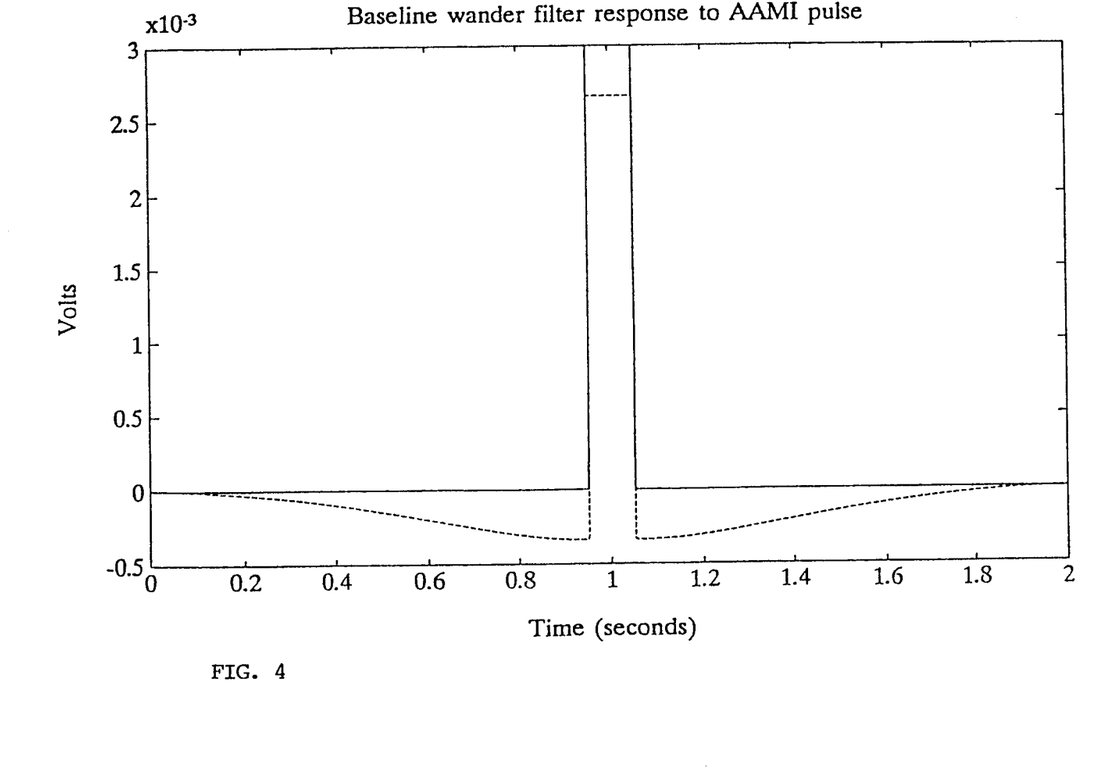
FIG. 4 illustrates the response of the filter of the preferred embodiment to a pulse input.

FIG. 4 illustrates the response of the forward and reverse filtering performed by system 10 to a pulse which starts at zero rises to 0.003 volts and returns to zero again. The response is in dashed lines and occurs subsequent in time to the input pulse but is laid over the pulse to permit comparison of the two. Note that the reverse filtering process causes filter settling to be reflected both before and after the occurrence of the pulse. Forward filtering only of the input pulse results in settling occurring only after the occurrence of the pulse but also results in a nonlinear response even after the data has settled.

Figure 6:
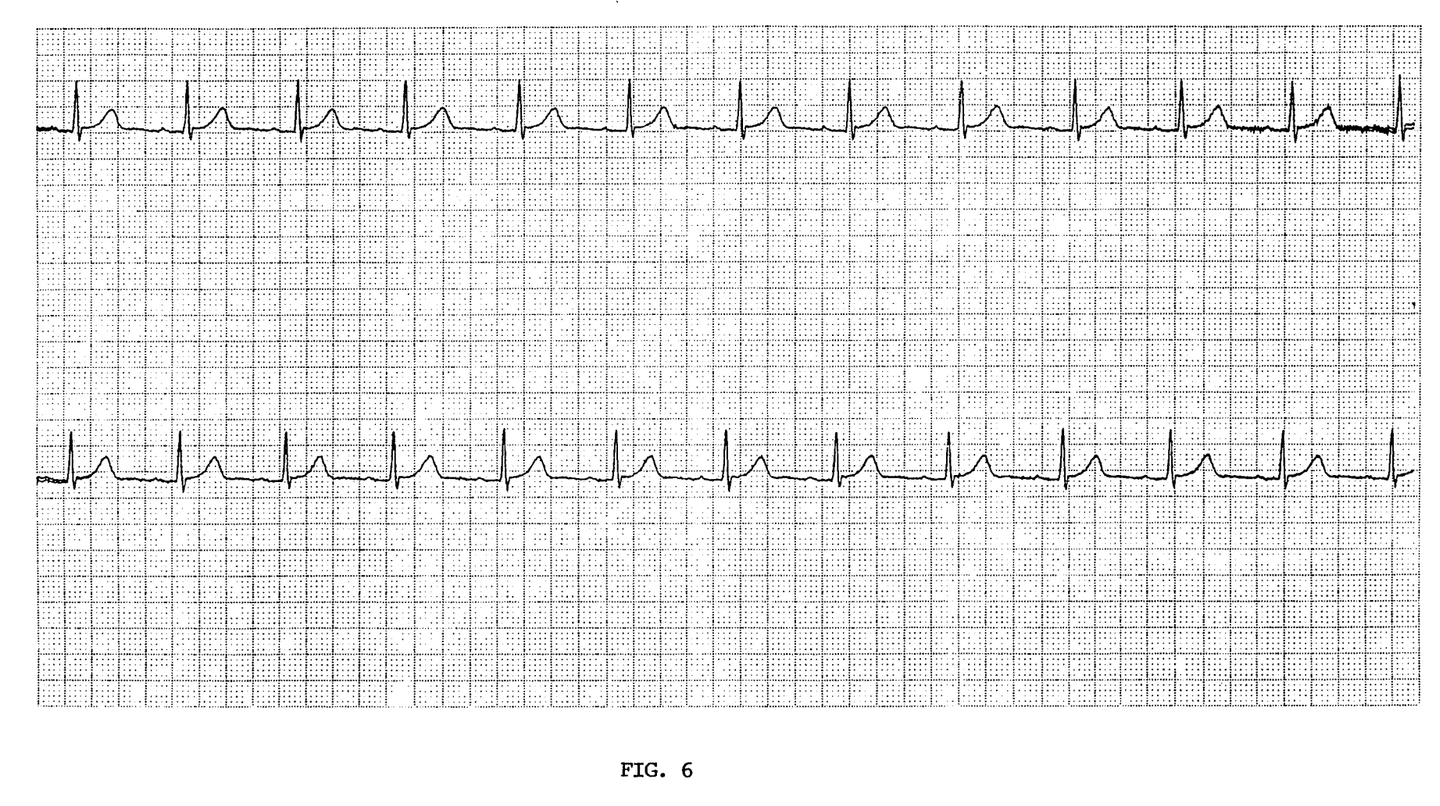
FIG. 6 comprises a plot of a test ECG signal and the same signal printed over the first signal after it is filtered in accordance with the present method.

In FIG. 6, what appears to be a single ECG waveform extending in chronological order from left to right and top to bottom is in fact one waveform printed on top of the other. FIG. 6 is the result of a test to check for distortion of the ECG signal in which an ideal ECG signal without baseline wander is applied to the input of converter 11 in system 10. This input signal and the output signal from queue 18, after operation as described above by system 10, are printed one over the other to illustrate that there is no distortion in the ECG waveform.

Figure 7:
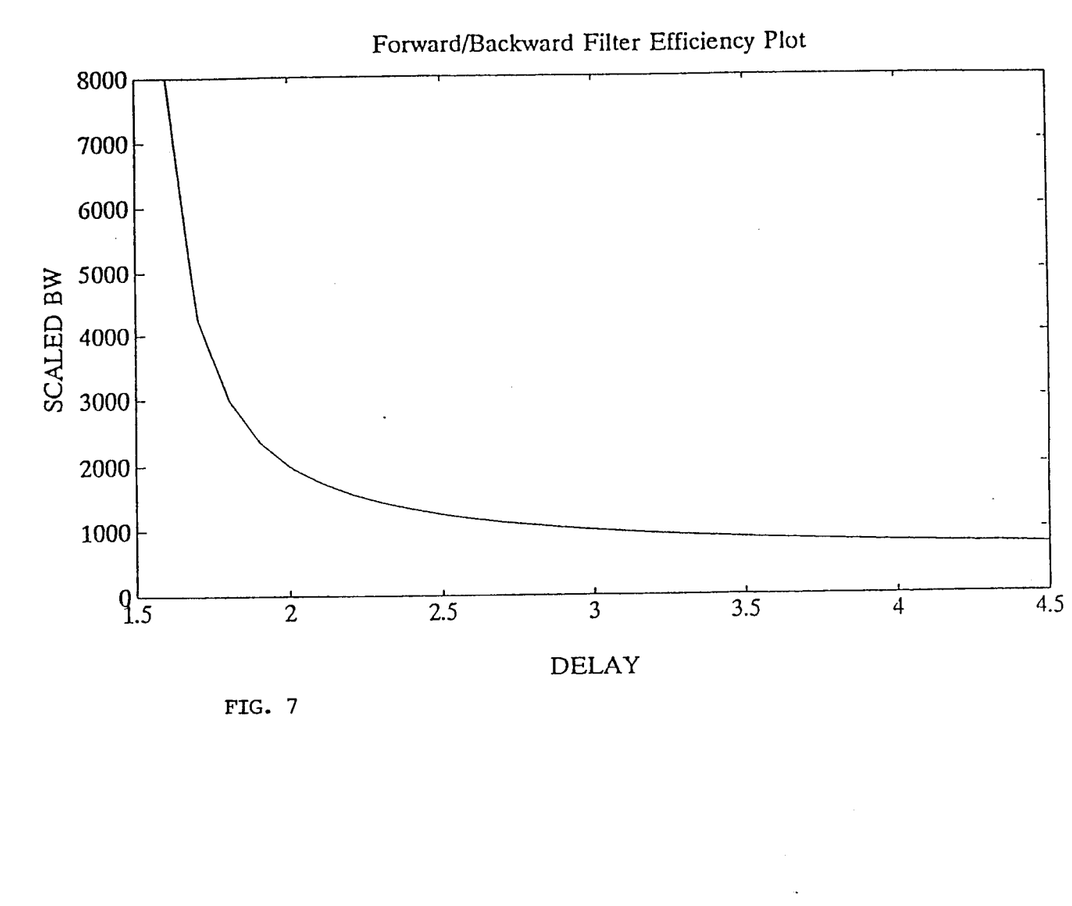
FIG. 7 shows the relationship between the settling time of the filter and the processor bandwidth required in the preferred embodiment.

FIG. 7 illustrates the relationship between time delay and processor bandwidth required to implement the preferred embodiment. The time delay is related to the length of the blocks, like blocks 28, 30, etc. in FIG. 2 which are reverse filtered as described above. The length of these data blocks is in turn related to the time it takes the filter to settle as this much data is discarded from the output of each reverse-filtered block. It can be seen that the minimum block size, and therefore delay until ECG data may be displayed, is 1.5 seconds plus one data point. The output of each block of data from reverse filter 16 will therefore produce one usable data point. For example, assume that an ECG waveform starts at t=0 seconds, that the length of each data block for reverse filtration is 4 seconds, rather than 3 seconds as in FIG. 2, and that the filter settling time remains at 1.5 seconds. The first block of reverse-filtered data produces filtered data from t=0 to t=2.5 seconds. The next block drawn from buffer 14 must therefore begin at t=2.5 seconds and extend to t=6.5 seconds thus producing filtered data through t=5 seconds in queue 18. The length of the data block selected for reverse filtration is therefore equal to the time delay between occurrence of the real-time ECG waveform and the display of the filtered waveform plus the filter settling time.

It should be appreciated that the method in which the filtered ECG waveform is to be displayed has a bearing on the amount of data which is to be disregarded after each data block passes through reverse filter 16. For example, monitor resolution is less than that provided by a print of an ECG waveform such as those in FIG. 5. While the filter settling time remains the same, it is possible to obtain satisfactory resolution on a monitor by disregarding a smaller portion of the initial output from filter 16 than if the output is to be printed.

On a monitor display, the delayed and filtered portion of the waveform may appear to the left of a length of real-time waveform equal to the amount of delay. A clinician can therefore observe the entire ECG waveform as it progresses across the monitor with the most current portion being unfiltered and real time and the remainder having baseline wander removed with the newest portion of the corrected waveform appearing after the delay produced by the filtration method of system 10.

Having illustrated and described the principles of our invention in a preferred embodiment thereof, it should be readily apparent to those skilled in the art that the invention can be modified in arrangement and detail without departing from such principles. We claim all modifications coming within the spirit and scope of the accompanying claims.

We claim:

1. A method for removing baseline wander from an ECG signal comprising the steps of:
    applying a real-time ECG signal to a first nonlinear filter which produces filtered-signal data;
    storing the filtered-signal data;
    applying blocks of the stored data in time-reversed order to a second nonlinear filter substantially identical to the first nonlinear filter thereby producing reverse-filtered blocks; and
    displaying each reverse-filtered block in chronological order.

2. The method of claim 1 wherein the second filter has a predetermined settling time and wherein said method further comprises the step of discarding a first time period of each reverse-filtered block substantially equal to the settling time of the second filter thereby retaining a second portion of each reverse-filtered block and wherein the step of displaying each reverse-filtered block in chronological order further comprises the step of displaying each second portion in chronological order.

3. The method of claim 2 wherein said predetermined settling time is approximately 1.5 seconds and wherein each block of stored data is equal to approximately 3 seconds of ECG data.

4. The method of claim 1 wherein the size of each block of stored data is the same for each block of stored data and wherein said method further comprises the step of discarding a first portion of each reverse-filtered block, said first portion comprising a substantially equal predetermined amount of data from the first part of each reverse-filtered block, prior to the step of displaying each reverse-filtered block in chronological order.

5. The method of claim 4 wherein the step of displaying each reverse-filtered block in chronological order comprises the step of displaying each one after the other so as to display a continuous ECG signal.

6. The method of claim 1 wherein the step of applying blocks of the stored data in time-reversed order to the nonlinear filter comprises the step of applying blocks which overlap in time.

7. A method for removing baseline wander from an ECG signal comprising the steps of:
   continuously filtering a real-time ECG signal thereby producing filtered ECG data;
   dividing the filtered data into predetermined time periods;
   reverse filtering the data in each time period; and
   arranging the reverse-filtered data in chronological order to form a continuous ECG signal.

8. The method of claim 7 wherein said method further includes the step of displaying the arranged data delayed in time relative to the real-time ECG signal.

9. The method of claim 8 wherein said predetermined time periods are overlapping and wherein the step of arranging the reverse-filtered data in chronological order to form a continuous ECG signal comprises the step of arranging a portion of the reverse-filtered data in each time period in chronological order to form a continuous ECG signal.

10. The method of claim 9 wherein each of said predetermined time periods overlaps another by the same amount and wherein the step of displaying the arranged data delayed in time relative to the real-time ECG signal comprises the step of delaying the arranged data delayed in time by an amount substantially equal to the time necessary to perform the step of reverse filtering the data in each time period plus the amount of time period overlap.

11. The method of claim 10 wherein the step of reverse filtering the data in each time period is performed by a filter having a predetermined settling time and wherein the amount of time period overlap is substantially equal to the settling time of said filter.

12. Apparatus for removing baseline wander from an ECG signal comprising:
   a first filter for continuously filtering a real-time ECG signal thereby producing filtered ECG data;
   means for dividing the filtered data into predetermined time periods;
   means for reverse filtering the data in each time period; and
   means for arranging the reverse-filtered data in chronological order to form a continuous ECG signal.

13. The apparatus of claim 12 wherein said apparatus further includes means for displaying the arranged data delayed in time relative to the real-time ECG signal.

14. The apparatus of claim 13 wherein said predetermined time periods are overlapping and wherein said means for arranging the reverse-filtered data in chronological order to form a continuous ECG signal comprises means for arranging a portion of the reverse-filtered data in each time period in chronological order to form a continuous ECG signal.

15. The apparatus of claim 14 wherein each of said predetermined time periods overlaps another by the same amount and wherein said means for displaying the arranged data delayed in time relative to the real-time ECG signal comprises means for displaying the arranged data delayed in time by an amount substantially equal to the time necessary to reverse filter the data in each time period plus the amount of time period overlap.

16. The apparatus of claim 15 wherein said filter has a predetermined settling time and wherein the amount of time period overlap is substantially equal to the settling time of said means for reverse filtering.

17. A method for removing baseline wander from an ECG signal comprising the steps of:
   filtering a real-time ECG signal according to a predetermined filter characteristic equation having a non-linear phase response to produce filtered-signal data;
   storing the filtered-signal data;
   filtering blocks of the stored data in time-reversed order according to the said filter characteristic equation thereby producing reverse-filtered blocks; and
   displaying each reverse-filtered block in chronological order.

18. A method according to claim 17 wherein said filtering the real-time ECG signal includes applying the real-time ECG signal to a first nonlinear filter and said filtering blocks of the stored data includes applying the blocks of the stored data to a second nonlinear filter substantially identical to the said first nonlinear filter.

* * * * *